(12) United States Patent
Wu et al.

(10) Patent No.: US 11,214,776 B2
(45) Date of Patent: Jan. 4, 2022

(54) PHYTASE MUTANT

(71) Applicant: QINGDAO VLAND BIOTECH GROUP CO., LTD., Qingdao (CN)

(72) Inventors: Xiuxiu Wu, Qingdao (CN); Huaming Wang, Qingdao (CN)

(73) Assignee: Qingdao Vland Biotech Group Co., Ltd., Qingdao (CN)

( * ) Notice: Subject to any disclaimer, the term of this patent is extended or adjusted under 35 U.S.C. 154(b) by 308 days.

(21) Appl. No.: 16/089,044

(22) PCT Filed: Aug. 8, 2016

(86) PCT No.: PCT/CN2016/093918
§ 371 (c)(1),
(2) Date: Sep. 27, 2018

(87) PCT Pub. No.: WO2017/166562
PCT Pub. Date: Oct. 5, 2017

(65) Prior Publication Data
US 2020/0277582 A1     Sep. 3, 2020

(30) Foreign Application Priority Data

Mar. 28, 2016  (CN) .......................... 201610184337.1

(51) Int. Cl.
*C12N 9/16* (2006.01)
*C12N 15/55* (2006.01)
*C12N 1/21* (2006.01)
*C12N 15/81* (2006.01)

(52) U.S. Cl.
CPC ............... *C12N 9/16* (2013.01); *C12N 15/81* (2013.01); *C12Y 301/03002* (2013.01)

(58) Field of Classification Search
None
See application file for complete search history.

(56) References Cited

U.S. PATENT DOCUMENTS

| | | | |
|---|---|---|---|
| 7,081,563 B2 | 7/2006 | Lanahan et al. | |
| 7,801,563 B2* | 9/2010 | Hara | H04B 7/0617 455/562.1 |
| 2013/0017185 A1* | 1/2013 | Maria | C12N 15/8243 424/94.6 |
| 2017/0022486 A1* | 1/2017 | Yao | C12N 1/14 |
| 2018/0002680 A1* | 1/2018 | Banerjee | C12N 9/16 |

FOREIGN PATENT DOCUMENTS

| | | |
|---|---|---|
| BR | 0215406 A | 9/2004 |
| CN | 101724611 A | 6/2010 |
| CN | 102392002 A | 3/2012 |
| CN | 102943083 A | 2/2013 |
| CN | 104404012 A | 3/2015 |
| CN | 104450643 A | 3/2015 |
| CN | 104911160 A | 9/2015 |
| CN | 105219749 A | 1/2016 |
| CN | 105624131 A | 6/2016 |
| WO | 03057248 A1 | 7/2003 |
| WO | WO-2016078168 A1 * | 5/2016 ............. C12N 15/70 |

OTHER PUBLICATIONS

Wang et al., Enzymology and thermal stability of phytase appA mutants, RSC Adv. 5, 2015, 43863-72. (Year: 2015).*

* cited by examiner

Primary Examiner — Robert B Mondesi
Assistant Examiner — Todd M Epstein
(74) Attorney, Agent, or Firm — Kilpatrick Townsend & Stockton LLP

(57) ABSTRACT

Provided are phytase mutants, preparation methods therefor and uses thereof, DNA molecule encoding each of the phytase mutants, a vector comprising the DNA molecule, and a host cell comprising the vector.

15 Claims, 1 Drawing Sheet
Specification includes a Sequence Listing.

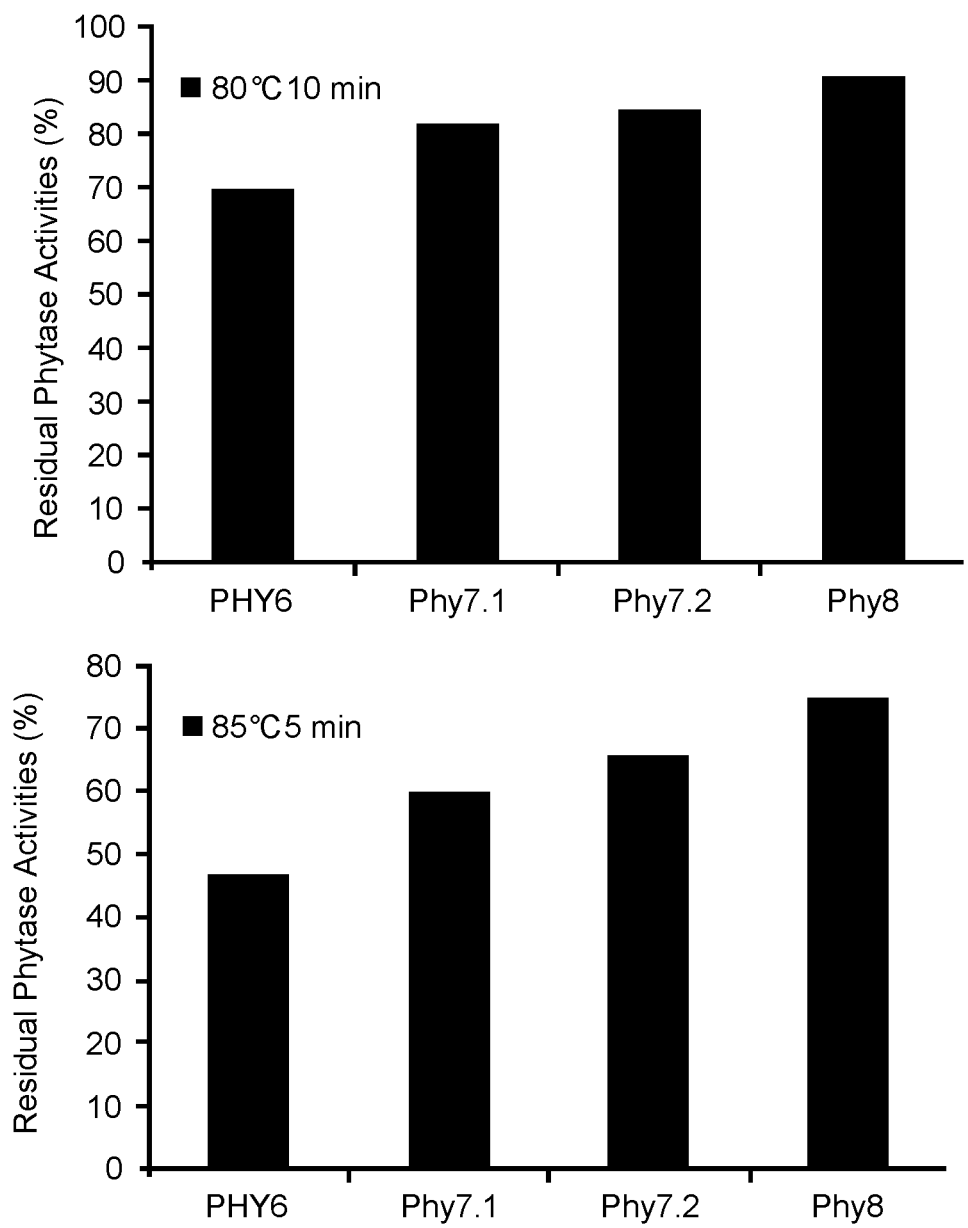

SEQUENCE LISTING

<160> NUMBER OF SEQ ID NOS: 12

<210> SEQ ID NO 1

<211> LENGTH: 410
<212> TYPE: PRT
<213> ORGANISM: Unknown
<220> FEATURE:
<223> OTHER INFORMATION: Phytase

<400> SEQUENCE: 1

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380
```

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 2
<211> LENGTH: 1233
<212> TYPE: DNA
<213> ORGANISM: Unknown
<220> FEATURE:
<223> OTHER INFORMATION: Phytase

<400> SEQUENCE: 2

```
cagagtgagc cggagctgaa gctggaaagt gtggtgattg tcagtcgtca tggtgtgcgt      60
gctccaacca aggccacgca actgatgcag gatgtcaccc cagacgcatg gccaacctgg     120
ccggtaaaac tgggttggct gacaccgcgc ggtggtgagc taatcgccta tctcggacat     180
taccaacgcc agcgtctggt agccgacgga ttgctggcga aaaagggctg cccgcagtct     240
ggtcaggtcg cgattattgc tgatgtcgac gagcgtaccc gtaaaacagg cgaagccttc     300
gccgccgggc tggcacctga ctgtgcaata accgtacata cccaggcaga tacgtccagt     360
cccgatccgt tatttaatcc tctaaaaact ggcgtttgcc aactggataa cgcgaacgtg     420
actgacgcga tcctcagcag ggcaggaggg tcaattgctg actttaccgg gcatcggcaa     480
acggcgtttc gcgaactgga acgggtgctt aattttccgc aatcaaactt gtgccttaaa     540
cgtgagaaac aggacgaaag ctgttcatta acgcaggcat taccatcgga actcaaggtg     600
agcgccgaca atgtctcatt aaccggtgcg gtaagcctcg catcaatgct gacggagata     660
tttctcctgc aacaagcaca gggaatgccg gagccggggt ggggaaggat caccgattca     720
caccagtgga acaccttgct aagtttgcat aacgcgcaat tttatttgct acaacgcacg     780
ccagaggttg cccgcagccg cgccaccccg ttattagatt tgatcaagac agcgttgacg     840
ccccatccac cgcaaaaaca ggcgtatggt gtgacattac ccacttcagt gctgtttatc     900
gccggacacg atactaatct ggcaaatctc ggcggcgcac tggagctcaa ctggacgctt     960
cccggtcagc cggataacac gccgccaggt ggtgaactgg tgtttgaacg ctggcgtcgg    1020
ctaagcgata acagccagtg gattcaggtt tcgctggtct tccagacttt acagcagatg    1080
cgtgataaaa cgccgctgtc attaaatacg ccgcccggag aggtgaaact gaccctggca    1140
ggatgtgaag agcgaaatgc gcagggcatg tgttcgttgg caggttttac gcaaatcgtg    1200
aatgaagcac gcataccggc gtgcagtttg taa                                 1233
```

<210> SEQ ID NO 3
<211> LENGTH: 410
<212> TYPE: PRT
<213> ORGANISM: Artificial sequence
<220> FEATURE:
<223> OTHER INFORMATION: synthesized

<400> SEQUENCE: 3

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln

```
                    50                  55                  60
Arg Leu Val Ala Asp Glu Leu Leu Pro Lys Cys Gly Cys Pro Gln Pro
 65                      70                  75                  80

Gly Gln Val Ala Ile Ile Ala Asp Val Asp Glu Arg Thr Arg Lys Thr
                     85                  90                  95

Gly Glu Ala Phe Ala Ala Gly Leu Ala Pro Asp Cys Ala Ile Thr Val
                    100                 105                 110

His His Gln Ala Asp Thr Ser Ser Pro Asp Pro Leu Phe Asn Pro Leu
                    115                 120                 125

Lys Thr Gly Val Cys Gln Leu Asp Val Ala Asn Val Thr Arg Ala Ile
130                     135                 140

Leu Glu Arg Ala Gly Gly Ser Ile Ala Asp Phe Thr Gly His Tyr Gln
145                     150                 155                 160

Pro Ala Phe Arg Glu Leu Glu Arg Val Leu Asn Phe Pro Gln Ser Pro
                    165                 170                 175

Leu Cys Leu Lys Arg Glu Lys Gln Asp Glu Pro Cys Ser Leu Thr Gln
                    180                 185                 190

Ala Leu Pro Ser Glu Leu Lys Val Ser Ala Asp Asn Val Ser Leu Thr
                    195                 200                 205

Gly Ala Val Ser Leu Ala Ser Met Leu Thr Glu Ile Phe Leu Leu Gln
210                     215                 220

Gln Ala Gln Gly Met Pro Glu Pro Gly Trp Gly Arg Ile Thr Asp Ser
225                     230                 235                 240

His Gln Trp Asn Thr Leu Leu Ser Leu His Asn Ala Gln Phe Asp Leu
                    245                 250                 255

Leu Gln Arg Thr Pro Glu Val Ala Arg Ser Arg Ala Thr Pro Leu Leu
                    260                 265                 270

Asp Leu Ile Lys Thr Ala Leu Thr Pro His Pro Pro Gln Lys Gln Ala
                    275                 280                 285

Tyr Gly Val Thr Leu Pro Thr Ser Val Leu Phe Ile Ala Gly His Asp
                    290                 295                 300

Thr Asn Leu Ala Asn Leu Gly Gly Ala Leu Glu Leu Asn Trp Thr Leu
305                     310                 315                 320

Pro Gly Gln Pro Asp Asn Thr Pro Pro Gly Gly Glu Leu Val Phe Glu
                    325                 330                 335

Arg Trp Arg Arg Leu Ser Asp Asn Ser Gln Trp Ile Gly Val Ser Leu
                    340                 345                 350

Val Phe Gln Thr Leu Gln Gln Met Arg Asp Lys Thr Pro Leu Ser Leu
                    355                 360                 365

Asn Thr Pro Pro Gly Glu Val Lys Leu Thr Leu Pro Gly Cys Glu Glu
                    370                 375                 380

Arg Asn Ala Gln Gly Met Cys Ser Leu Ala Gly Phe Thr Gln Ile Val
385                     390                 395                 400

Asn Glu Ala Arg Ile Pro Ala Cys Ser Leu
                    405                 410

<210> SEQ ID NO 4
<211> LENGTH: 1233
<212> TYPE: DNA
<213> ORGANISM: Artificial sequence
<220> FEATURE:
<223> OTHER INFORMATION: synthesized

<400> SEQUENCE: 4
cagtcagaac cagagttgaa gttggagtca gtcgtcatcg ttagtagaca tggagttaga    60
```

-continued

```
gcccctacaa aggctaccca gcttatgcaa gatgttaccc cagacgcttg gccaacttgg    120
cctgtcaagt tgggagaact tactcctaga ggtggagagt tgattgccta ccttggtcat    180
tattggagac aaagattggt tgcagatgaa ttgcttccaa agtgtggttg ccctcaacca    240
ggacaggttg caattatcgc tgatgttgat gaaagaacta gaaaaacagg agaggctttt    300
gctgccggat tggccccaga ttgtgcaatc actgttcatc accaagccga tacatcttcc    360
ccagacccct tgttcaaccc tcttaagaca ggagtctgtc agttggatgt tgccaatgtc    420
accagagcaa ttttggaaag agctggtgga agtatcgccg actttactgg tcactaccaa    480
ccagctttca gagaattgga gagttcttaa ctttccac agtccccatt gtgtcttaag    540
agagaaaagc aagatgagcc atgcagtttg actcaggctc ttccttctga gttgaaagtt    600
tccgccgaca acgtctcatt gaccggagct gtttctcttg cctccatgtt gactgaaatt    660
ttcttgcttc aacaggctca gggtatgcca gagcctggtt ggggaagaat caccgatagt    720
catcagtgga cactttgct ttctttgcac aatgctcaat cgacttgct tcagagaact    780 ccagaagttg caagatccag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt tggagcttaa ctggacattg    960
ccaggtcaac ctgataatac cccacctggt ggagaattgg tttttgagag atggagaaga    1020
ttgtcagaca atagtcaatg gattcaggtt ccttggtct tccaaacttt gcaacagatg    1080
agagataaga caccattgtc acttaacacc ccacctggtg aagtcaaatt gacacttcct    1140
ggatgtgaag agagaaatgc acaaggaatg tgcagtcttg ctggtttcac ccaaatcgtc    1200
aatgaggcta gaatccctgc ttgttccttg taa                                  1233
```

<210> SEQ ID NO 5
<211> LENGTH: 410
<212> TYPE: PRT
<213> ORGANISM: Artificial sequence
<220> FEATURE:
<223> OTHER INFORMATION: synthesized

<400> SEQUENCE: 5

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asp Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
```

```
                    145                 150                 155                 160
        Pro Ala Phe Arg Glu Leu Glu Arg Val Leu Asn Phe Pro Gln Ser Pro
                        165                 170                 175
        Leu Cys Leu Lys Arg Glu Lys Gln Asp Glu Pro Cys Ser Leu Thr Gln
                        180                 185                 190
        Ala Leu Pro Ser Glu Leu Lys Val Ser Ala Asp Asn Val Ser Leu Thr
                        195                 200                 205
        Gly Ala Val Ser Leu Ala Ser Met Leu Thr Glu Ile Phe Leu Leu Gln
                    210                 215                 220
        Gln Ala Gln Gly Met Pro Glu Pro Gly Trp Gly Arg Ile Thr Asp Ser
        225                 230                 235                 240
        His Gln Trp Asn Thr Leu Leu Ser Leu His Asn Ala Gln Phe Asp Leu
                        245                 250                 255
        Leu Gln Arg Thr Pro Glu Val Ala Arg Ser Arg Ala Thr Pro Leu Leu
                        260                 265                 270
        Asp Leu Ile Lys Thr Ala Leu Thr Pro His Pro Pro Gln Lys Gln Ala
                        275                 280                 285
        Tyr Gly Val Thr Leu Pro Thr Ser Val Leu Phe Ile Ala Gly His Asp
                    290                 295                 300
        Thr Asn Leu Ala Asn Leu Gly Gly Ala Leu Glu Leu Asn Trp Thr Leu
        305                 310                 315                 320
        Pro Gly Gln Pro Asp Asn Thr Pro Gly Gly Glu Leu Val Phe Glu
                        325                 330                 335
        Arg Trp Arg Arg Leu Ser Asp Asn Ser Gln Trp Ile Gln Val Ser Leu
                        340                 345                 350
        Val Phe Gln Thr Leu Gln Gln Met Arg Asp Lys Thr Pro Leu Ser Leu
                        355                 360                 365
        Asn Thr Pro Pro Gly Glu Val Lys Leu Thr Leu Pro Gly Cys Glu Glu
                        370                 375                 380
        Arg Asn Ala Gln Gly Met Cys Ser Leu Ala Gly Phe Thr Gln Ile Val
        385                 390                 395                 400
        Asn Glu Ala Arg Ile Pro Ala Cys Ser Leu
                        405                 410

<210> SEQ ID NO 6
<211> LENGTH: 1233
<212> TYPE: DNA
<213> ORGANISM: Artificial sequence
<220> FEATURE:
<223> OTHER INFORMATION: synthesized

<400> SEQUENCE: 6
cagtcagaac cagagttgaa gttggagtca gtcgtcatcg ttagtagaca tggagttaga      60 gccccctacaa aggctaccca gcttatgcaa gatgttaccc cagacgcttg gccaacttgg    120
cctgtcaagt tgggagaact tactcctaga ggtggagagt tgattgccta ccttggtcat    180
tattggagac aaagattggt tgcagatgaa ttgcttccaa gtgtggttg ccctcaacca     240 ggacaggttg caattatcgc tgatgttgat gaaagaacta gaaaaacagg agaggctttt    300
gctgccggat tggccccaga ttgtgcaatc actgttcatc accaagccga tacatcttcc    360
ccagaccctt tgttcgaccc tcttaagaca ggagtctgtc agttggatgt tgccaatgtc    420
accagagcaa ttttggaaag agctggtgga agtatcgccg actttactgg tcactaccaa    480 ccagcttttca gagaattgga gagagttctt aactttccac agtccccatt gtgtcttaag    540
agagaaaagc aagatgagcc atgcagtttg actcaggctc ttccttctga gttgaaagtt    600
```

```
tccgccgaca acgtctcatt gaccggagct gtttctcttg cctccatgtt gactgaaatt    660
ttcttgcttc aacaggctca gggtatgcca gagcctggtt ggggaagaat caccgatagt    720
catcagtgga acactttgct ttctttgcac aatgctcaat tcgacttgct tcagagaact    780
ccagaagttg caagatccag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt tggagcttaa ctggacattg    960
ccaggtcaac ctgataatac cccacctggt ggagaattgg tttttgagag atggagaaga   1020
ttgtcagaca atagtcaatg gattcaggtt tccttggtct tccaaacttt gcaacagatg   1080
agagataaga caccattgtc acttaacacc ccacctggtg aagtcaaatt gacacttcct   1140
ggatgtgaag agagaaatgc acaaggaatg tgcagtcttg ctggtttcac ccaaatcgtc   1200
aatgaggcta gaatccctgc ttgttccttg taa                                1233
```

<210> SEQ ID NO 7
<211> LENGTH: 410
<212> TYPE: PRT
<213> ORGANISM: Artificial sequence
<220> FEATURE:
<223> OTHER INFORMATION: synthesized

<400> SEQUENCE: 7

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Pro Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
```

```
            245                 250                 255
Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Pro Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410
```

<210> SEQ ID NO 8
<211> LENGTH: 1233
<212> TYPE: DNA
<213> ORGANISM: Artificial sequence
<220> FEATURE:
<223> OTHER INFORMATION: synthesized

<400> SEQUENCE: 8

```
cagtcagaac cagagttgaa gttggagtca gtcgtcatcg ttagtagaca tggagttaga      60
gccctacaa aggctaccca gcttatgcaa gatgttaccc cagacgcttg gccaacttgg      120
cctgtcaagt tgggagaact tactcctaga ggtggagagt tgattgccta ccttggtcat     180
tattggagac aaagattggt tgcagatgaa ttgcttccaa agtgtggttg ccctcaacca     240
ggacaggttg caattatcgc tgatgttgat gaaagaacta gaaaaacagg agaggctttt     300
gctgccggat tggccccaga ttgtgcaatc actgttcatc accaagccga tacatcttcc     360
ccagaccctt tgttcaaccc tcttaagaca ggagtctgtc agttggatgt tgccaatgtc     420
accagagcaa ttttggaaag agctggtgga agtatcgccg actttactgg tcactaccaa     480
ccagctttca gagaattgga gagagttctt aactttccac agtccccatt gtgtcttaag     540
agagaaaagc aagatgagcc atgcagtttg actcaggctc ttccttctga gttgaaagtt     600
tccgccgaca acgtctcatt gaccggagct tggtctcttg cctccatgtt gactgaaatt     660
ttcttgcttc aacaggctca gggtatgcca gagcctggtt ggggaagaat caccgatagt     720
catcagtgga acactttgct ttctttgcac aatgctcaat tcgacttgct tcagagaact     780
ccagaagttg caagatccag agctacacct ttgcttgatc ttattaagac cgcattgact     840
ccacatccac ctcaaaaaca ggcttatgga gttacattgc ctacctctgt cttgttcatc     900
gctggtcacg acactaactt ggcaaatctt ggtggagctt tggagcttaa ctggacattg     960
ccaggtcaac ctgataatac cccacctggt ggagaattgg tttttgagag atggagaaga    1020
ttgtcagaca atagtcaatg gattcaggtt ccttggtct tccaaacttt gcaacagatg    1080
agagataaga caccattgtc acttaacacc ccacctggtg aagtcaaatt gacacttcct    1140
```

```
ggatgtgaag agagaaatgc acaaggaatg tgcagtcttg ctggtttcac ccaaatcgtc    1200
aatgaggcta gaatccctgc ttgttccttg taa                                 1233
```

<210> SEQ ID NO 9
<211> LENGTH: 410
<212> TYPE: PRT
<213> ORGANISM: Artificial sequence
<220> FEATURE:
<223> OTHER INFORMATION: synthesized

<400> SEQUENCE: 9

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asp Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Pro Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
```

```
            340                 345                 350
Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 10
<211> LENGTH: 1233
<212> TYPE: DNA
<213> ORGANISM: Artificial sequence
<220> FEATURE:
<223> OTHER INFORMATION: synthesized

<400> SEQUENCE: 10
cagtcagaac cagagttgaa gttggagtca gtcgtcatcg ttagtagaca tggagttaga      60 gccctacaa  aggctaccca gcttatgcaa gatgttaccc cagacgcttg gccaacttgg     120
cctgtcaagt tgggagaact tactcctaga ggtggagagt tgattgccta ccttggtcat    180
tattggagac aaagattggt tgcagatgaa ttgcttccaa agtgtggttg ccctcaacca    240
ggacaggttg caattatcgc tgatgttgat gaaagaacta gaaaacagg agaggctttt     300 gctgccggat tggccccaga ttgtgcaatc actgttcatc accaagccga tacatcttcc    360
ccagaccctt tgttcgaccc tcttaagaca ggagtctgtc agttggatgt tgccaatgtc    420
accagagcaa ttttggaaag gctggtgga agtatcgccg actttactgg tcactaccaa    480
ccagctttca gagaattgga gagttctt aactttccac agtccccatt gtgtcttaag     540
agagaaaagc aagatgagcc atgcagtttg actcaggctc ttccttctga gttgaaagtt   600
tccgccgaca acgtctcatt gaccggagct tggtctcttg cctccatgtt gactgaaatt   660
ttcttgcttc aacaggctca gggtatgcca gagcctggtt ggggaagaat caccgatagt   720
catcagtgga acactttgct ttcttttgcac aatgctcaat cgacttgct tcagagaact    780 ccagaagttg caagatccag agctacacct tgcttgatc ttattaagac cgcattgact    840
ccacatccac tcaaaaaca ggcttatgga gttacattgc ctacctctgt cttgttcatc    900
gctggtcacg acactaactt ggcaaatctt ggtggagctt tggagcttaa ctggacattg    960
ccaggtcaac tgataatac cccacctggt ggagaattgg tttttgagag atggagaaga   1020
ttgtcagaca atagtcaatg gattcaggtt tccttggtct tccaaacttt gcaacagatg   1080
agagataaga caccattgtc acttaacacc ccacctggtg aagtcaaatt gacacttcct   1140
ggatgtgaag agagaaatgc acaaggaatg tgcagtcttg ctggtttcac ccaaatcgtc   1200
aatgaggcta gaatccctgc ttgttccttg taa                                1233

<210> SEQ ID NO 11
<211> LENGTH: 32
<212> TYPE: DNA
<213> ORGANISM: Artificial sequence
<220> FEATURE:
<223> OTHER INFORMATION: synthesized

<400> SEQUENCE: 11
ggcgaattcc agtcagaacc agagttgaag tt                                   32
```

```
<210> SEQ ID NO 12
<211> LENGTH: 32
<212> TYPE: DNA
<213> ORGANISM: Artificial sequence
<220> FEATURE:
<223> OTHER INFORMATION: synthesized

<400> SEQUENCE: 12
atagcggccg cttacaagga acaagcaggg at                                    32
```

PHYTASE MUTANT

CROSS-REFERENCE TO RELATED APPLICATIONS

This application is a U.S. National Phase application under 35 U.S.C. § 371 of International Application No. PCT/CN2016/093918, filed Aug. 8, 2016, which claims priority to Chinese application No. 201610184337.1, named "Phytase Mutant", filed on Mar. 28, 2016, the contents of which are hereby incorporated by reference in their entirety.

REFERENCE TO A "SEQUENCE LISTING" SUBMITTED AS ASCII TEXT FILES

The Sequence Listing written in file 1102462_SEQ.TXT, created on Jan. 29, 2020, 26,365 bytes, machine format IBM-PC, MS-Windows operating system, in accordance with 37 C.F.R. §§ 1.821- to 1.825, is hereby incorporated by reference in its entirety for all purposes.

FIELD OF THE INVENTION

The present invention relates to biotechnology field, and particularly relates to phytase mutants, the method of producing the mutants and the uses thereof. The present invention also relates to DNA molecules encoding the mutants, expression vectors and host cells.

BACKGROUND OF THE INVENTION

Phytase is a type of phosphatase enzyme and can hydrolyze phytate phosphorus (myo-inositol hexakisphosphate) into myo-inositol and inorganic phosphate. There are two types of phytase: 3-phytase (EC 3.1.3.8) and 6-phytase (EC 3.1.2.6). Phytase is widely spread in nature, occurring in plants, animals and microorganisms, including higher plants such as maize and wheat, prokaryotic microbes such as *Bacillus subtilis, Pseudomonas, Lactobacillus* and *Escherichia coli* and eukaryotic microbes.

Phytate phosphorus is a major component of all plant seeds, constituting 1%-3% by weight of many cereals, beans and oil seeds and typically accounting for 60%-80% of the total phosphorus. However, mono gastric animals metabolize only 0%-40% of the phytate phosphorus since they lack digestive enzymes for phytate, which results in a number of problems. First of all, phosphorus source are wasted. On the one hand, phytate phosphorus source in feed cannot be efficiently utilized; on the other hand, in order to ensure that the animals' requirement for phosphorus, it is necessary to add inorganic phosphorus in feed, which increases the feed costs. Secondly, the excreta with high phosphorus pollute the environment. 85% of the phytate phosphorus in feed will be directly excreted by animals, and the excreta containing high phytate phosphorus can lead to significant water and soil pollution. In addition, phytate phosphorus is also a kind of antinutrient, which binds to several metallic ions such as $Zn^{2+}$, $Ca^{2+}$, $Cu^{2+}$ and $Fe^{2+}$ and other proteins to form insoluble compositions, preventing or inhibiting the absorption of the nutrients in the gastrointestinal tract, and reduces the effective utilization of nutrients.

Phytase can be used as a feed additive for mono gastric animals, and the feeding effect has been confirmed worldwide. Phytase can improve the phosphorus availability of plant feeds by 60% and decrease the phosphorus excretion by 40%. Phytase also can counteract the anti-nutritional properties of phytate. Therefore, the addition of phytase in animal feed is helpful for improving the production efficiency of livestock and poultry industry and for reducing the environmental pollution caused by phytate.

There are two main kinds of phytase for industrial production, one of which is fungal phytase derived from *Aspergillus niger* and the other is bacterial phytase derived from *E. coli*. The phytase APPA derived from *E. coli* has high specific activity and good gastrointestinal stability, and can be used in the feed industry by addition to mash feed directly or spraying on pelleted feed.

Bacterial phytase APPA has lower heat stability, the retention rate of which was even less than 30% after being kept at 70 degree Celsius (° C.) for 5 minutes in water bath. Thus there is a restriction of adding phytase directly into feed processing due to its low tolerance to high temperature of 80-90° C. in feed pelleting period. However, there are still several disadvantages of applying liquid spraying technology using phytase, such as high equipment cost, less stability and uniformity of enzymes in the feed. Therefore it is of great importance to improve the thermostability of phytase for feed.

SUMMARY OF THE INVENTION

This invention provides a phytase mutant and a method of production thereof. The thermostability of the phytase mutant is significantly improved, which is conducive to the wide applications of the phytase mutant in feed field.

In order to achieve the above objects, the invention provides the following technical solutions:

This invention provides a phytase mutant comprising the amino acid sequence shown as (I) or (II) or (III):

(I) an amino acid sequence which has at least 70% identity to the amino acid sequence of SEQ ID NO: 1;

(II) an amino acid sequence which has at least one immune epitope of the phytase, and comprises a modification, a substitution, a deletion, and/or an insertion of one or more amino acids within the amino acid sequence of the phytase;

(III) an amino acid sequence encoded by a nucleotide sequence of SEQ ID NO: 2, or a nucleotide sequence the complementary strand of which hybridizes to SEQ ID NO: 2, or a nucleotide sequence which differs from the sequence of SEQ ID NO: 2 due to the degeneracy of the genetic code;

wherein the amino acid sequence comprises 1, 2, 3, 4, 5, 6, 7, 8, 9, 10, 11, 12, 13, 14, 15, 16, 17 or 18 amino acid substitutions.

In some embodiments of the invention, the phytase mutant comprises amino acid sequence which has at least 75% identity to the amino acid sequence of SEQ ID NO: 1.

In some embodiments, the phytase mutant comprises amino acid sequence which has at least 80% identity to the amino acid sequence of SEQ ID NO: 1.

In some embodiments, the phytase mutant comprise amino acid sequence which has at least 85% identity to the amino acid sequence of SEQ ID NO: 1

In some embodiments, the phytase mutant comprises amino acid sequence which has at least 90% identity to the amino acid sequence of SEQ ID NO: 1

In some embodiments, the phytase mutant comprises amino acid sequence which has at least 95% identity to the amino acid sequence of SEQ ID NO: 1

In some embodiments of the invention, the modifications include amidation, phosphorylation, methylation, acetylation, ubiquitination, glycosylation or carbonylation.

In some embodiments of the invention, the phytase mutant comprises 16 or 17 or 18 amino acid substitutions.

In some embodiments, the phytase mutant comprises one or more amino acid substitutions at a position selected from positions 46, 62, 70, 73, 75, 80, 114, 137, 142, 146, 159, 161, 176, 187, 255 or 380.

In some embodiments, the phytase mutant comprises amino acid substitutions at positions 46, 62, 70, 73, 75, 80, 114, 137, 142, 146, 159, 161, 176, 187, 255 and/or 380.

In some embodiments, the amino acid sequence of the phytase is SEQ ID NO: 1, and the polynucleotide sequence encoding the phytase is SEQ ID NO: 2.

In some embodiments, the amino acid sequence of the phytase mutant is SEQ ID NO: 3 or SEQ ID NO: 5 or SEQ ID NO: 7 or SEQ ID NO: 9.

The invention also provides a DNA molecule encoding the phytase mutant.

In some embodiments, the polynucleotide sequence of the DNA molecule encoding phytase mutant is SEQ ID NO: 4 or SEQ ID NO: 6 or SEQ ID NO: 8 or SEQ ID NO: 10.

The invention also provides a vector comprising the DNA molecule encoding the phytase mutant.

In further embodiments, the amino acid substitution is from Trp to Glu at position 46, from Gln to Trp at position 62, from Gly to Glu at position 70, from Ala to Pro at position 73, from Lys to Cys at position 75, from Ser to Pro at position 80, from Thr to His at position 114, from Asn to Val at position 137, from Asp to Arg at position 142, from Ser to Glu at position 146, from Arg to Tyr at position 159, from Thr to Pro at position 161, from Asn to Pro at position 176, from Ser to Pro at position 187, from Tyr to Asp at position 255, and from Ala to Pro at position 380, the position corresponding to the respective position in SEQ ID NO: 1.

The amino acid sequence of the phytase mutant above is SEQ ID NO: 3 and one polynucleotide sequence encoding the phytase mutant is SEQ ID NO: 4.

The invention also provides a plasmid comprising the polynucleotide sequence of SEQ ID NO: 4.

In other embodiments, the phytase mutant also comprises the amino acid substitutions at positions 126 and/or 211.

In other embodiments, the phytase mutant also comprises the amino acid substitution at position 126.

In other embodiments, the amino acid substitution is from Asn to Asp at position 126 of SEQ ID NO: 3.

The amino acid sequence of the phytase mutant above is SEQ ID NO: 5 and one polynucleotide sequence encoding the phytase mutant is SEQ ID NO: 6.

The invention also provides a plasmid comprising the polynucleotide sequence of SEQ ID NO: 6.

In other embodiments, the phytase mutant also comprises the amino acid substitution at position 211.

In other embodiments, the amino acid substitution is from Val to Trp at position 211 of SEQ ID NO: 3.

The amino acid sequence of the phytase mutant above is SEQ ID NO: 7 and one polynucleotide sequence encoding the phytase mutant is SEQ ID NO: 8.

The invention also provides a plasmid comprising the polynucleotide sequence of SEQ ID NO: 8.

In other embodiments, the phytase mutant also comprises the amino acid substitutions at positions 126 and 211.

In other embodiments, the amino acid substitutions are from Asn to Asp at position 126 and from Val to Trp at position 211 of SEQ ID NO: 3.

The amino acid sequence of the phytase mutant above is SEQ ID NO: 9 and one polynucleotide sequence encoding the phytase mutant is SEQ ID NO: 10.

The invention also provides a plasmid comprising the polynucleotide sequence of SEQ ID NO: 10.

The invention also provides a method of producing the phytase mutant, which includes:

Step 1: obtain a DNA molecule comprising a polynucleotide sequence encoding the amino acid sequence shown as (I) or (II) or (III):

(I) an amino acid sequence which has at least 70% identity to the amino acid sequence of the phytase;

(II) an amino acid sequence which has at least one immune epitope of the phytase, and comprise a modification, a substitution, a deletion, and/or an insertion of one or more amino acids of the amino acid sequence of the phytase;

(III) an amino acid sequence encoded by a nucleotide sequence of SEQ ID NO: 2, or a nucleotide sequence the complementary strand of which hybridizes to SEQ ID NO: 2, or a nucleotide sequence which differs from the sequence of SEQ ID NO: 2 due to the degeneracy of the genetic code;

wherein the amino acid sequence comprises 1, 2, 3, 4, 5, 6, 7, 8, 9, 10, 11, 12, 13, 14, 15, 16, 17 or 18 amino acid substitutions.

Step 2: fuse the DNA molecule obtained by step 1 to an expression vector, construct recombinant expression vector, and transform the recombinant expression vector into a host cell;

Step 3: induce the host cell comprising recombinant expression vector to express the fusion protein, and then isolate and purify the fusion protein.

In some embodiments, the modifications include amidation, phosphorylation, methylation, acetylation, ubiquitination, glycosylation, or carbonylation.

In some embodiments, the substitutions in the method include one or more amino acid substitutions at a position selected from positions 46, 62, 70, 73, 75, 80, 114, 137, 142, 146, 159, 161, 176, 187, 255 or 380.

In some embodiments, the substitutions in the method are at positions 46, 62, 70, 73, 75, 80, 114, 137, 142, 146, 159, 161, 176, 187, 255 and/or 380.

In other embodiments, the substitutions in the method also comprise amino acid substitutions at positions 126 and/or 211.

In some embodiments, the DNA molecule in step 1 of the method is obtained by amplification reactions of cDNA encoding the amino acid sequence of SEQ ID NO:3 or SEQ ID NO:5 or SEQ ID NO:7 or SEQ ID NO:9.

The host cell in Step 2 of the method is *Pichia*.

This invention also provides the applications of the phytase mutants described herein: (1) an animal feed comprising an effective amount of a phytase mutant of this invention to improve animal digestion and absorption of phosphorus; and (2) a method for improving animal digestion and absorption of phosphorus comprising adding an effective amount of the phytase mutant into an animal feed before feeding to the animal.

This invention also provides a host cell comprising the recombinant expression vector.

In some embodiments, the host cell is *Pichia*.

The thermostability of the phytase mutant expressed in the *Pichia* comprising the recombinant vector is significantly improved.

This invention provides a phytase mutant, comprising the amino acid sequence shown as (I) or (II) or (III):

(I) an amino acid sequence which has at least 70% identity to the amino acid sequence of the phytase;

(II) an amino acid sequence which has at least one immune epitope of the phytase, and comprises a modification, a substitution, a deletion, and/or an insertion of one or more amino acids within the amino acid sequence of the phytase;

(III) an amino acid sequence encoded by a nucleotide sequence of SEQ ID NO: 2, or a nucleotide sequence the complementary strand of which hybridizes to SEQ ID NO: 2, or a nucleotide sequence which differs from the sequence of SEQ ID NO: 2 due to the degeneracy of the genetic code; wherein the amino acid sequence comprises 1, 2, 3, 4, 5, 6, 7, 8, 9, 10, 11, 12, 13, 14, 15, 16, 17 or 18 amino acid substitutions.

Using the phytase PHY6 as a basis, the invention provides an additional one-point mutant Phy7.1 (N126D), an additional one-point mutant Phy7.2 (V211W), and an additional two-point mutant Phy8 (N126D and V211W). After being treated at 80° C. for 10 min, the residual enzyme activities of the mutants Phy7.1, Phy7.2 and Phy8 are 12.48%, 15.50% and 20.90% higher, respectively, compared with that of PHY6. After being treated at 85° C. for 5 min, the residual enzyme activities of the mutants Phy7.1, Phy7.2 and Phy8 are 13.05%, 18.50% and 27.56% higher, respectively. The heat resistance of these mutants is significantly higher than that of PHY6, which will improve the applications of the phytase mutants in feed.

BRIEF DESCRIPTION OF THE DRAWINGS

FIG. 1 shows the thermostabilities of Phy7.1, Phy7.2 and Phy8.

EXAMPLES

In order to improve the thermostability of wild phytase APPA (the amino acid sequence shown as SEQ ID NO: 1, and the polynucleotide sequence shown as SEQ ID NO: 2), 16 amino acid substitutions (W46E, Q62W, G70E, A73P, K75C, S80P, T114H, N137V, D142R, S146E, R159Y, T161P, N176P, S187P, Y255D and A380P) were introduced into APPA. The phytase mutant obtained was named PHY6, of which the amino acid sequence was SEQ ID NO: 3 and the encoding polynucleotide sequence was SEQ ID NO: 4. Compared with APPA, the heat resistance of PHY6 was significantly improved. (This part of contents has been described in details in Chinese application No. 201510532520.1, named "Phytase mutants", filed on Aug. 26, 2015.)

The invention discloses a phytase mutant, a method of production and a use thereof, a DNA molecule encoding the mutant, a vector, and a host cells. The invention has described the method and application in the preferred embodiments, and technicians in this field can readily modify or appropriately modify and combine the methods and applications to realize and apply the invention without departing from the contents, spirit and scope of the invention.

Conventional techniques and methods in the field of genetic engineering and molecular biology are used in the invention, for example, the methods recorded in MOLECULAR CLONING: A LABORATORY MANUAL, 3nd Ed. (Sambrook, 2001) and CURRENT PROTOCOLS IN MOLECULAR BIOLOGY (Ausubel, 2003). These general references provide one of skill in art with a general dictionary of many of the terms used in this invention. Based on the technical scheme described in the invention, all technical and scientific terms can choose other conventional methods, experimental programs and reagents to realize the invention, including, but not limited to that described in the embodiments of the invention. For example, the following experimental materials and reagents can be used in the invention:

Strains and vectors: E. coli DH5α, Pichia pastoris strain GS115, vector pPIC9k, Amp and G418 were purchased from Invitrogen.

Enzymes and Kits: PCR enzymes and ligases were purchased from Takara; restriction endonucleases were purchased from Fermentas; plasmid mini kit and gel extraction kit were purchased from Omega; geneMorph II random mutagenesis kit was purchased from MBL Beijing Biotech Co., Ltd.

Medium Recipes:
Lariant broth (LB medium): 0.5% yeast extract, 1% tryptone, 1% NaCl, pH7.0;
LB-AMP medium: LB medium with 100 μg/mL ampicillin;
Yeast extract peptone dextrose medium (YPD medium): 1% yeast extract, 2% tryptone, 2% glucose;
Minimal dextrose medium (MD medium): 2% tryptone, 2% agar;
BMGY medium: 2% tryptone, 1% yeast extract, 100 mM potassium phosphate buffer (pH 6.0), 1.34% YNB, $4 \times 10^{-5}$ biotin, 1% glycerol;
BMMY medium: 2% tryptone, 1% yeast extract, 100 mM potassium phosphate buffer (pH 6.0), 1.34% YNB, $4 \times 10^{-5}$ biotin, 1% methanol.

The invention is further illustrated by the following examples:

Example 1 Screening for Thermostable Mutants

In order to improve the thermostability of phytase mutant PHY6, the protein structure of PHY6 (encoded by the polynucleotide sequence shown as SEQ ID NO: 4) was analyzed. There were two domains in the protein: domain I contained 134 amino acid residues at the N-terminus and 152 amino acid residues at C-terminus, while domain II contained the remaining 124 amino acid residues in the middle. The conserved sequences and activity center were all in domain I. Without destroying the secondary structure and activity center of the protein, further mutations of the amino acid residuals were carried out.

1.1 Design of PCR primers PHY6-F1 and PHY6-R1
PHY6-F1: GGC<u>GAATTC</u> CAGTCAGAACCAGAGTT-GAAGTT (Underlined is the recognition site of restriction endonuclease EcoRI), which is shown as SEQ ID NO: 11;
PHY6-R1: ATA<u>GCGGCCGC</u>TTACAAGGAACAAGCAGGGAT (Underlined is the recognition site of restriction endonuclease NotI), which is shown as SEQ ID NO: 12;

PHY6 gene (shown as SEQ ID NO: 4) was amplified using the primers above by a GeneMorph II random mutagenesis kit (Stratagene). After being recovered, the amplification products were digested with EcoRI and NotI and ligated into EcoRI-NotI-digested plasmid pET21a. After that the plasmid was transformed into E. coli BL21 (DE3) and then the recombinant E. coli cells were spread onto LB+Amp plates. After being incubated at 37° C., the colonies were transferred by a toothpick one by one into 96-well polypropylene microtiter plates containing LB+Amp medium with 150 ul 0.1 mM IPTG in each well. The microtiter plates were incubated at 37° C. for 6 h with shaking at 220 rpm. The supernatant was removed from the fermentation broth by centrifugation. Afterwards the cells were re-suspended with buffer and repeated freeze-thawed to obtain phytase-containing E. coli cell lysates.

40 ul cell lysates were transferred into two separate new 96-well plates, one of which was treated at 80° C. for 10 min, and the other was not. 80 ul substrates were added into each well of the plates and incubated for 30 min at 37° C. Afterwards 80 ul stop solution (ammonium vanadate:ammonium molybdate:nitric acid=1:1:2) was added to end the reaction. In each well of the plates, the contents of inorganic phosphate were determined, which reflected the post-heat treatment activities of different mutants obtained in the invention.

Compared with phytase PHY6, the thermostabilities of some mutants are not improved. The thermostabilities or activities of some mutants are even worse. Besides, there are some mutants with improved thermostabilities, but their enzymatic properties are significantly changed, which also limits their applications in feed. Finally, this invention provides three phytase mutants with significantly improved thermostability without negative effects on their high activities and original enzymatic properties: N126D, V211W, and N126D/V211W.

One mutant is named Phy7.1 with one-point mutation N126D, its amino acid sequence is shown as SEQ ID NO: 5, and the encoding polynucleotide sequence is shown as SEQ ID NO: 6.

Another phytase mutant is named Phy7.2 with one-point mutation V211W, its amino acid sequence is shown as SEQ ID NO: 7, and the encoding polynucleotide sequence is shown as SEQ ID NO: 8.

The other phytase mutant is named Phy8 with two-point mutation N126D and V211W, its amino acid sequence is shown as SEQ ID NO: 9, and the encoding polynucleotide sequence is shown as SEQ ID NO: 10.

1.2 Synthesis and Amplification of Mutant Genes

The polynucleotide sequences of PHY6 and three phytase mutants were synthesized with reference to SEQ ID NO: 4, SEQ ID NO: 6, SEQ ID NO: 8 and SEQ ID NO: 10 and optimized based on codon preference of *Pichia Postoris* by Shanghai Generay Biotech Co., Ltd, of which an EcoRI restriction site and a NotI restriction site were added to the 5' end and 3' end respectively.

1.3 Construction of Expression Vector

The four polynucleotide sequences synthesized in 1.2 and the plasmids pPIC-9k were first digested by EcoRI and NotI, and then ligated together at 16° C. overnight respectively. After that, the recombinant plasmid was transformed into *E. coli* DH5α. The recombinant *E. coli* cells then were spread onto LB+Amp plates. The plates were placed inverted and incubated at 37° C. until transformants grew up. Positive transformants were selected and verified by colony PCR and DNA sequencing. The reaction system of colony PCR contained: monoclonal sample, rTaqDNA polymerase 0.5 ul, 10×Buffer 2.0 μL, dNTPs (2.5 mM) 2.0 μL, 5'AOX primer (10M): 0.5 μL, 3'AOX primer: 0.5 μL, ddH$_2$O 14.5 μL; PCR conditions were: 95° C. for 5 min(1 cycle), 94° C. for 30 sec, 55° C. for 30 sec, 72° C. for 2 min(30 cycles) and 72° C. for 10 min(1 cycle). The expression vector with PHY6 gene shown as SEQ ID NO: 4 was named as pPIC9K-PHY6, and three vectors with mutant genes shown as SEQ ID NO: 6, SEQ ID NO: 8, SEQ ID NO: 10 were named as pPIC9K-Phy7.1, pPIC9K-Phy7.2 and pPIC9K-Phy8 respectively.

1.4 Construction of the Recombinant *P. pastoris* Strain 1.4.1 Preparation of Competent *P. pastoris* Cells Host cells *P. pastoris* GS115 were spread onto YPD plates and the plates were incubated at 30° C. for 48 h. GS115 colonies were picked up and inoculated into 6 mL YPD liquid medium for approximately 12 h at 30° C. with shaking at 220 rpm. Then the YPD liquid medium containing GS115 was inoculated into 30 mL YPD liquid medium and incubated for 5 h at 30° C. with shaking at 220 rpm. The cell density of the yeast cultures were measured using a spectrophotometer. When the optical density (OD600) between 1.1 and 1.3, 4 mL yeast cultures were added into a sterilized EP tubes and centrifuged at 9000 rpm and 4° C. for 2 min. The supernatants were removed and aspirated off by sterile filter paper, while the remaining yeast cells were re-suspended in 1 ml of sterile pre-cooled water. The suspension containing yeast cells was centrifuged at 9000 rpm and 4° C. for 2 min. The supernatants were removed, while the remaining yeast cells were re-suspended in 1 ml of sterile water again. The suspension containing yeast cells was centrifuged at 9000 rpm and 4° C. for 2 min. The supernatant was removed, while the remaining yeast cells were re-suspended in 1 ml of pre-cooled sorbitol (1 mol/L). The sorbitol containing yeast cells was centrifuged at 9000 rpm and 4° C. for 2 min. Then the supernatant was removed, while the remaining yeast cells were re-suspended in 100-150 μl of sterile pre-cooled sorbitol (1 mol/L).

1.4.2 Transformation and Screening

The recombinant plasmids pPIC9K-PHY6, pPIC9K-Phy7.1, pPIC9K-Phy7.2 and pPIC9K-Phy8 were linearized by Sal I and transformed into host cells *Pichia pastoris* GS115 respectively by electroporation. The recombinant *P. pastoris* strains GS115/pPIC9K-PHY6, GS115/pPIC9K-Phy7.1, GS115/pPIC9K-Phy7.2 and GS115/pPIC9K-Phy8 were screened on MD plates. And then multiple copies of transformants were screened on YPD plates containing different concentrations of geneticin (0.5 mg/mL-8 mg/mL).

One of the transformants of the recombinant strains GS115/pPIC9K-PHY6 was named *Pichia pastoris* PHY6. One of the transformants of the recombinant strains GS115/pPIC9K-Phy7.1 was named *Pichia pastoris* Phy7.1. One of the transformants of the recombinant strains GS115/pPIC9K-Phy7.2 was named *Pichia pastoris* Phy7.2. One of the transformants of the recombinant strains GS115/pPIC9K-Phy8 was named *Pichia pastoris* Phy8. The four transformants above were first inoculated into separate flasks with BMGY medium and cultured at 30° C. for 1d with agitation at 250 rpm, and then inoculated in BMMY medium at 30° C. for 4 d with agitation at 250 rpm. 0.5% methanol was added into the medium as an inducer every 24 h. The cells were removed from the fermentation broth by centrifugation at 9000 rpm for 10 min and the fermentation supernatants containing phytase PHY6, or phytase Phy7.1 or phytase Phy7.2 or Phy8 were retained.

(1) Definition of Phytase Activity Unit

One phytase unit is the activity of phytase that generates 1 micromole of inorganic phosphorus per minute from 5.0 mmol/L sodium phytate at pH 5.0 and 37° C., which is indicated as U.

(2) Method for Detecting Phytase Activity 1.8 mL of acetic acid buffer (pH 5.0) and 0.2 mL of sample are both added into two separate cuvettes A and B, mixed and warmed at 37° C. for 5 min. 4 mL of substrate solution is added into cuvette A and 4 mL of stop solution is added into cuvette B, mixed and reacted at 37° C. for 30 min. The reaction is ended by adding and mixing 4 mL stop solution in cuvette A and 4 mL substrate solution in cuvette B. After standing for 10 min, the absorbance is measured at 415 nm. Three repeats are made for each sample, and the average of the absorbance values is used for calculating the phytase activity by regression linear.

Enzyme activity: $X = F \times C/(m \times 30)$ where: X—Unit of enzyme activity, U/g(mL);

F—Total dilution factors of sample solution before reaction;

C—The enzyme activity calculated from the linear regression equation based on the absorbance of the actual sample solution, U;

m—Sample mass or volume, g/mL;

30—Reaction time;

Phytase activities of the fermentation supernatants of *Pichia pastoris* PHY6, Phy7.1, Phy7.2 and Phy 8 were detected by the method mentioned above, and the results are provided in Table 1.

TABLE 1

Phytase Activities

| Sample | Value 1 | Value 2 | Value 3 | Average | Activity (U/mL) |
|---|---|---|---|---|---|
| PHY6 | 0.491 | 0.487 | 0.490 | 0.489 | 241 |
| Phy7.1 | 0.472 | 0.467 | 0.470 | 0.470 | 223 |
| Phy7.2 | 0.470 | 0.463 | 0.466 | 0.466 | 205 |
| Phy8 | 0.485 | 0.479 | 0.483 | 0.482 | 237 |

The phytase activities of the fermentation supernatants of *Pichia pastoris* PHY6, *Pichia pastoris* Phy7.1, *Pichia pastoris* Phy7.2 and *Pichia pastoris* Phy8 are 241 U/mL, 223 U/mL, 205 U/mL and 237 U/mL, respectively.

1.5 Fermentation Process

*Pichia pastoris* PHY6, *Pichia pastoris* Phy7.1, *Pichia pastoris* Phy7.2 and *Pichia pastoris* Phy8 were cultured in four separate 10 μL fermenters with the fermentation medium containing: 1.1 g/L CaSO$_4$, 5.5 g/L KH$_2$PO$_4$, 55 g/L NH$_4$H$_2$PO$_4$, 16.4 g/L MgSO$_4$, 20.3 g/L K$_2$SO$_4$, 1.65 g/L KOH and 0.05% antifoam.

The fermentation parameters: pH 5.0, 30° C., agitation at 300 rpm, aeration at 1.0-1.5 v/v, and the dissolved oxygen kept above 20%.

There were three stages of the fermentation process. The first stage was for cell culture with 7% seed inoculated and cultured at 30° C. for 24-26 h until the supplement of glucose was finished. The second stage was for cell starvation with no more carbon source supplemented. This stage lasted about 30-60 min until the concentration of dissolved oxygen rose to 80%. The third stage was for inducing the expression of phytase with methanol added as an inducer in flow, and the concentration of dissolved oxygen maintained at more than 20%, which lasted about 150-180 h. After that, the fermentation broth was treated by the filter press to obtain crude enzyme solution.

The phytase activities of the crude enzyme solutions were determined by the method mentioned in 1.4.2, and the results are provided in Table 2.

TABLE 2

Phytase Activities

| Sample | Value 1 | Value 2 | Value 3 | Average | Activity (U/mL) |
|---|---|---|---|---|---|
| PHY6 | 0.488 | 0.487 | 0.490 | 0.488 | 11403 |
| Phy7.1 | 0.475 | 0.478 | 0.480 | 0.478 | 10807 |
| Phy7.2 | 0.469 | 0.473 | 0.470 | 0.471 | 10713 |
| Phy8 | 0.483 | 0.480 | 0.481 | 0.481 | 11133 |

The phytase activities of the crude enzyme solutions of *Pichia pastoris* PHY6, *Pichia pastoris* Phy7.1, *Pichia pastoris* Phy7.2 and *Pichia pastoris* Phy8 are 11403 U/mL, 10807 U/mL, 10713 U/mL and 11133 U/mL, respectively.

1.6 Analysis of enzymatic properties 1.6.1 Optimal Temperature

The phytase activities of the crude enzyme solutions of *Pichia pastoris* PHY6, i *Pichia pastoris* Phy7.1, *Pichia pastoris* Phy7.2 and *Pichia pastoris* Phy8 were measured at pH5.5 and 5° C. intervals between 30° C. and 85° C. With the highest phytase activity calculated 100%, the relative enzyme activities were calculated.

The results show that the optimal temperatures of phytase mutant Phy7.1, Phy7.2 and Phy8 are all 75° C., which is the same with phytase mutant PHY6.

1.6.2 Optimal pH

The crude enzyme solutions of *Pichia pastoris* PHY6, *Pichia pastoris* Phy7.1, *Pichia pastoris* Phy7.2 and *Pichia pastoris* Phy8 were diluted by 0.1M acetic acid-sodium acetate buffer at pH 2.0, 2.5, 3.0, 3.5, 4.0, 4.5, 5.0, 5.5, 6.0, 6.5, 7.0 respectively. The phytase activities were measured at 37° C., and the relative enzyme activities were calculated with the highest enzyme activity calculated 100%.

The results show that the optimal pH of *Pichia pastoris* Phy7.2 and *Pichia pastoris* PHY6 is both 5.0, but the optimal pH of *Pichia pastoris* Phy7.1 and *Pichia pastoris* Phy8 is reduced by 0.5 unit, to 4.5.

1.6.3 Thermostability

The crude enzyme solutions of *Pichia pastoris* PHY6, *Pichia pastoris* Phy7.1, *Pichia pastoris* Phy7.2 and *Pichia pastoris* Phy8 were diluted 10 times with 0.25M sodium acetate buffer (pH 5.0) which was preheated for 10 min. The diluted enzyme solutions were well mixed and treated at 85° C. for 5 min, and 80° C. for 10 min. The phytase activities were measured when the diluted enzyme solutions were cooled to room temperature. With the phytase activity of the untreated enzyme solution calculated 100%, the residual phytase activities were calculated.

As shown in FIG. 1, compared with phytase PHY6, the residual activities of phytase mutants Phy7.1, Phy7.2 and Phy8 are 12.48%, 15.50% and 20.90% higher, respectively, after being treated at 80° C. for 10 min, and are 13.05%, 18.50% and 27.56% higher, respectively, after being treated at 85° C. for 5 min. The heat-resistance of phytase mutants Phy7.1, Phy7.2 and Phy8 are higher than that of phytase PHY6 (P<0.01).

In conclusion, using the phytase PHY6 as a basis, the invention provides an one-point mutant Phy7.1 (N126D), an one-point mutant Phy7.2 (V211W) and a two-point mutant Phy8 (N126D and V211W). Compared with phytase PHY6, the optimal temperature of the phytase mutants Phy7.1, Phy7.2 and Phy8 remains unchanged, meanwhile the optimal pH of the phytase mutants Phy7.2 remains unchanged, but the optimal pH of Phy7.1 and Phy8 is reduced by 0.5 unit. The thermostabilities of the phytase mutants Phy7.1, Phy7.2 and Phy8 have been significantly improved (P<0.01), which is conducive to the applications of the phytase mutants in feed.

The invention claimed is:

1. A phytase mutant, comprising an amino acid sequence having at least 70% sequence identity to the amino acid sequence of SEQ ID NO: 1, which comprises substitutions of the amino acids at positions 46, 62, 70, 73, 75, 80, 114, 137, 142, 146, 159, 161, 176, 187, 255 and 380 and further comprises one or two substitutions at positions 126 and 211.

2. The phytase mutant of claim 1, wherein the amino acid substitution at position 46 is from Trp to Glu, at position 62 is from Gln to Trp, at position 70 is from Gly to Glu, at position 73 is from Ala to Pro, at position 75 is from Lys to Cys, at position 80 is from Ser to Pro, at position 114 is from Thr to His, at position 137 is from Asn to Val, at position 142 is from Asp to Arg, at position 146 is from Ser to Glu, at position 159 is from Arg to Tyr, at position 161 is from Thr to Pro, at position 176 is from Asn to Pro, at position 187 is from Ser to Pro, at position 255 is from Tyr to Asp, and at position 380 is from Ala to Pro.

3. The phytase mutant of claim 1, wherein the amino acid substitution at position 126 is from Asn to Asp and at position 211 is from Val to Trp.

4. The phytase mutant of claim 1, comprising the amino acid sequence of SEQ ID NO: 5.

5. The phytase mutant of claim 1, comprising the amino acid sequence of SEQ ID NO: 7.

6. The phytase mutant of claim 1, comprising the amino acid sequence of SEQ ID NO: 9.

7. A nucleic acid comprising a polynucleotide sequence encoding the phytase mutant of claim 1.

8. The nucleic acid of claim 7, wherein the polynucleotide sequence comprises the sequence of SEQ ID NO: 6.

9. The nucleic acid of claim 7, wherein the polynucleotide sequence comprises the sequence of SEQ ID NO: 8.

10. The nucleic acid of claim 7, wherein the polynucleotide sequence comprises the sequence of SEQ ID NO: 10.

11. An expression vector comprising a polynucleotide sequence encoding the phytase mutant of claim 1.

12. A host cell comprising the expression vector of claim 11.

13. A method of producing a phytase mutant comprising:
Step 1: obtain a nucleic acid comprising a polynucleotide sequence encoding a phytase mutant comprising an amino acid sequence having at least 70% sequence identity to the amino acid sequence of SEQ ID NO: 1, which comprises amino acid substitutions at positions 46, 62, 70, 73, 75, 80, 114, 137, 142, 146, 159, 161, 176, 187, 255 and 380 and further comprises one or two substitutions at positions 126 and 211;
Step 2: fuse the nucleic acid obtained by step 1 to an expression vector, construct recombinant expression vector, and transform the recombinant expression vector into a host cell; and
Step 3: induce the host cell comprising recombinant expression vector to express the phytase mutant, and then isolate and purify the phytase mutant.

14. The method of claim 13, wherein the phytase mutant comprises the amino acid sequence of SEQ ID NO: 5, 7, or 9.

15. The method o claim 13, wherein the polynucleotide sequence comprises the sequence of SEQ ID NO: 6, 8, or 10.

* * * * *